(12) United States Patent
Mammone et al.

(10) Patent No.: US 6,413,525 B1
(45) Date of Patent: Jul. 2, 2002

(54) METHODS OF EXFOLIATION USING N-ACETYL GLUCOSAMINE

(75) Inventors: Thomas Mammone, Farmingdale; David C. Gan, Huntington Station, both of NY (US)

(73) Assignee: Color Access, Inc., Melville, NY (US)

( * ) Notice: Subject to any disclaimer, the term of this patent is extended or adjusted under 35 U.S.C. 154(b) by 0 days.

(21) Appl. No.: 09/306,314

(22) Filed: May 6, 1999

(51) Int. Cl.[7] ................................................. A61K 7/48
(52) U.S. Cl. ...................... 424/401; 424/78.03; 514/62; 514/886; 514/937; 514/944
(58) Field of Search .............................. 424/401, 78.03; 514/944, 937, 886, 62

(56) References Cited

U.S. PATENT DOCUMENTS

| | | | |
|---|---|---|---|
| 5,215,759 A | * | 6/1993 | Mausner |
| 5,866,142 A | | 2/1999 | Riordan |
| 5,874,463 A | * | 2/1999 | Ancira |
| 6,147,054 A | | 11/2000 | Ambrosi |
| 6,159,485 A | | 12/2000 | Yu et al. |

FOREIGN PATENT DOCUMENTS

| | | |
|---|---|---|
| EP | 0 852 946 | 7/1998 |
| JP | 59013708 | 1/1984 |
| JP | 8188526 | 7/1996 |
| WO | 97/12597 | 10/1997 |
| WO | 98/52576 | 11/1998 |

OTHER PUBLICATIONS

Roeder, G., *Total Health*, vol. 16, No. 2, p. 30, 1994.*

Brysk, M. M., et al., "Glycoproteins modulate adhesion in terminally differentiated keratinocytes", Cell and Tissue Research (1988) 253, pp. 657–663.

* cited by examiner

*Primary Examiner*—Raj Bawa
(74) *Attorney, Agent, or Firm*—Dorene M. Prise, Esq.

(57) ABSTRACT

The present invention relates to a method of exfoliating and moisturizing the skin comprising the steps of topically applying a cosmetic or pharmaceutical composition. The composition comprises an amino sugar, N-acetyl-D-glucosamine and related compounds.

10 Claims, No Drawings

METHODS OF EXFOLIATION USING N-ACETYL GLUCOSAMINE

FIELD OF THE INVENTION

The present invention relates to methods of substantially exfoliating the skin. In particular, the invention relates to topically applied compositions containing an amino sugar in the form of N-acetyl glucosamine.

BACKGROUND OF THE INVENTION

This invention relates to methods of using N-acetyl glucosamine to exfoliate the skin. The cells of the outermost layer of the stratum corneum are constantly shed naturally, by the normal process of desquamation, as minute particles. When fully keratinised tissue loses its cellular structure and reaches the surface of the stratum corneum, it breaks up into microscopic squames and sheds off the surface of the skin. Microscopic squames at the skin surface are commonly referred to as dead skin cells and make up a dead skin layer on the skin surface. The process of desquamation has been estimated to cause a loss of tissue in an amount of up to 14 grams per day. This loss is constantly replenished with cells from lower layers of the epidermis. Thus, the layers of the epidermis are composed of cells moving up towards the surface in successive stages of differentiation until death when they are finally sloughed off and lost to the environment. Desquamation is one of the processes by which skin maintains its health and vitality as nutrients and moisture are continuously replaced on the surface of the skin when dead skin cells are removed. Normally, the desquamation process takes about 14 days (i.e., the corneocyte takes 14 days to reach the outermost layer of the strateum corneum to be shed). When desquamation does not take place regularly, the surface of the skin tends to become rougher and more wrinkles and other undesirable effects appear on the surface of the skin. However, in addition to or as an alternative to the natural desquamation process, exfoliation is often used to rejuvenate and enhance the health of the skin.

Exfoliation is a technique whereby dead skin cells are removed or sloughed from the skin surface to promote a healthier and more youthful appearance to the skin. Several compounds are known to be useful as exfoliants such as for example, alpha hydroxy acid ("AHA"), beta hydroxy acid ("BHA"), retinoic acid ("retin A"), and enzymes. An exfoliant such as AHA breaks the bond holding individual squames together and allows them to detach and shed.

Producing a variety of alternatives for exfoliation is desirable because skin types vary among consumers and therefore, having a variety of exfoliants available to meet various individual skincare needs of consumers is beneficial. Thus, there is a continued effort to find additional alternative ways of aiding the sloughing ability of the skin and promoting its health for various types of skin. This is, therefore, an object of the present invention.

SUMMARY OF THE INVENTION

The present invention relates to a method for exfoliating the skin by topically applying pharmaceutical or cosmetic compositions containing an exfoliating-effective amount of N-acetyl-D-glucosamine, N-acetylgalactosamine, or a combination thereof. This method provides a natural alternative to the exfoliation process that is as effective as other typical exfoliation techniques.

DETAILED DESCRIPTION OF THE INVENTION

It has now been unexpectedly discovered that topically applied N-acetyl-D-glucosamine or N-acetylgalactosamine containing compositions exfoliate the skin. Combinations of N-acetyl-D-glucosamine and N-acetylgalactosamine can also be used. These compositions which exfoliate the skin can also include chitin to enhance the process of exfoliation.

It is known that amino sugars are capable of modulating the adhesion of keratinocytes, in vitro. It is disclosed by Brysk, M. in "Glycoproteins modulate adhesion in terminally differentiated keratinocytes," that N-acetylglucosamine, N-acetylneuraminic acid and N-acetylgalactosamine are involved in the dissociation of aggregates of glycoproteins that bind corneocytes together. Specifically, amino sugars are known to inhibit the reaggregation of corneocytes which have been dissociated into single squames by homogenization in ether. Further, amino sugars in the form of N-acetylglucosamine have been used as an oral nutrient supplement in conjunction with other topical cosmetic products, such as for example, products offered by Life-Force, Inc. which include N-acetyl-D-glucosamine in the form of a pill taken as a nutritional supplement. However, it is not suggested in the prior art to formulate a pharmaceutical or cosmetic composition for topical application to the skin using N-acetylglucosamine as an exfoliant. In fact, in WO97/12597 it is disclosed that when studied to determine its efficacy as a topical desquamating agent, N-acetyl-D-glucosamine was not found to be effective. The exfoliant in WO97/12597 is a compound comprising a chain of carbohydrates linked by a linking moiety to an alkyl or alkenyl chain. Further, WO97/12597, incorporated herein by reference, only includes N-acetyl-D-glucosamine as one of the units forming the carbohydrate portion which is linked by the linking moiety to the alkyl or alkenyl chain for desquamation of the skin. It is not disclosed in WO97/12597 that N-acetyl-D-glucosamine alone can exfoliate the skin.

Compositions for topical application containing N-acetyl-D-glucosamine have been disclosed for example, in JP 59013708, WO 98/152576, and U.S. Pat. No. 5,866,142, each incorporated herein by reference. To soften and moisturize the skin, a cosmetic containing an N-acetyl amino sugar is disclosed in JP 59013708. A composition for alleviating itching and pain containing N-acetyl-D-glucosamine is disclosed in WO 98/52576. In U.S. Pat. No. 5,866,142, a composition for exfoliating the skin has been disclosed, which includes N-acetyl-D-glucosamine. The presence of N-acetyl-D-glucosamine contributes to enhancing the amount of hyaluronic acid which the skin naturally produces in greater quantities in response to exfoliation, induced by other compounds such as histidine. However, no exfoliating activity is attributed to N-acetyl-D-glucosamine. A cosmetic composition containing N-acetylglucosamine and having good adhesion to the skin (i.e., does not lift off of the skin) is disclosed in JP 8188526. However, the prior art does not disclose the ability of glucosamine, and particularly, N-acetyl-D-glucosamine, to exfoliate the skin.

The composition of the present invention contains an exfoliating-effective amount of N-acetyl-D-glucosamine, N-acetylgalactosamine, or a combination thereof. By the term "exfoliating-effective amount," as used in the present specification, is meant an amount which is effective to cause exfoliation of the skin. The amount of N-acetyl-D-glucosamine, N-acetylgalactosamine, or a combination thereof, in the present invention will vary depending on the desired strength or intensity of exfoliation. The N-acetyl-D-glucosamine or N-acetylgalactosamine is present in the composition in an amount of about 0.01 to about 25.0 percent of the weight of the composition; preferably 0.5 to about 10.0 percent, and more preferably about 1.0 to 5.0 percent of the weight of the composition.

The N-acetyl-D-glucosamine or N-acetylgalactosamine per se is added directly to the cosmetic or pharmaceutical composition by admixing; alternatively, extracts of materials containing substantial quantities of N-acetylglucosamine or N-acetylgalactosamine as a component can be used to provide the same concentration. These compositions can also contain chitin. The amounts of chitin in the composition are also present in exfoliating-effective amounts as previously described.

The intensity of exfoliation can also be controlled by the frequency with which the compositions are applied to the skin and the compositions are applied periodically for a period of time sufficient to exfoliate the skin. Accordingly, the compositions are applied to the skin for a period of at least 2 months, and preferably for at least 4 months, during which time the compositions are applied on a weekly basis. However, a preferred method of obtaining the benefits of the composition is via chronic topical application of the composition to exfoliate the skin. It is suggested, as an example, that "chronic" application be within a range of from about once per week to about 4 to 5 times weekly, preferably daily, most preferably twice daily. By "chronic" application, it is meant herein that the period of topical application may be over the lifetime of the user, preferably for a period of at least about 6 months to about 20 years, more preferably from about 1 year to about 10 years, and still more preferably from about 2 years to about 5 years, thereby resulting in regular desquamation, which may aid in reducing the appearance of fine lines and wrinkles due to chronological aging or photoaging.

The method of the present invention may include applying in addition to the exfoliating effective amount of N-acetyl-D-glucosamine or N-acetylgalactosamine, other optional components, depending on the intended end use of the compositions. These include, but are not limited to, additional exfoliants, preservatives, fragrances, emollients, antiseptics, antiinflammatories, antibacterials, stabilizers, antioxidants, vitamins, pigments, dyes, humectants, and propellants, as well as other classes of materials the presence of which in the compositions may be cosmetically, medicinally, or otherwise desired. Such components can be found in the CTFA International Cosmetics Ingredients Dictionary. Examples of additional exfoliants include but are not limited to chemical exfoliants such as AHAs, for example, lactic acid, or BHAs, for example, salicylic acid, or physical exfoliants such as pumice, polyethylene, walnut shell powder, and the like, or combinations thereof. The amount of additional exfoliants alone or in combination will depend on the type of exfoliant and the strength of exfoliation desired. Preservatives employed, may be in an amount of from about 0.01 to about 2.00 percent, preferably from about 0.02 to about 1.00 percent, of the formula weight. Examples of suitable preservatives are BHA, BHT, propyl paraben, butyl paraben or methyl paraben or an isomer, homolog, analog or derivative thereof.

For topical application, according to the method of the present invention, the compositions can also be formulated with a variety of cosmetically and/or pharmaceutically acceptable vehicles. Accordingly, the compositions of the present invention comprise a pharmaceutically or cosmetically acceptable carrier, in an amount appropriate to accommodate the other components of the formulation. The term "pharmaceutically and/or cosmetically acceptable vehicle" refers to a base, for either pharmaceutical or cosmetic use, within which N-acetyl-D-glucosamine or N-acetylgalactosamine is soluble and which will not cause harm to humans or other recipients. As used herein, "pharmaceutical" or "cosmetic" will be understood to encompass both human and animal pharmaceuticals or cosmetics. There are few limitations on the type of base which is suitable for the compositions containing N-acetyl-D-glucosamine or N-acetylgalactosamine. The vehicle may be aqueous, non-aqueous or a combination thereof appropriate for the formulation desired.

The compositions can be prepared in any form convenient for topical application to the skin. Such forms include, but are not limited to, gels, creams, dispersions, emulsions (water-in-oil or oil-in-water), suspensions, creams, lotions, gels, foams, mousses and the like. In a preferred embodiment, the carrier is a suspension, dispersion or emulsion. The emulsion may be an oil-in-water emulsion, or a water-in-oil emulsion. These emulsions contain one or more oil components, an aqueous component, and a specific emulsifier component chosen depending on the nature of the desired emulsion.

The invention is further illustrated by the following non-limiting examples.

EXAMPLE 1

A composition, according to the present invention is prepared as follows:

| Material | Weight % |
|---|---|
| Phase I | |
| Purified Water | 54.2 |
| Sodium Dehydroacetate | 0.1 |
| Pantethine | 0.1 |
| Germall 115 | 0.5 |
| Sodium Hyaluronate | 0.2 |
| Purified Water | 4.0 |
| Steareth-20 | 3.0 |
| Purified Water | 10.0 |
| N-acetyl-D-Glucosamine | 1.0 |
| Cystamine Bis-Lactamide | 0.3 |
| Dimethicone | 5.0 |
| Cyclomethicone | 15.0 |
| Tocopheryl Acetate | 0.5 |
| Polyacrylamide | 2.0 |
| Butylene Glycol | 1.0 |
| Purified Water | 2.0 |
| Citric Acid | 0.1 |

To prepare the composition, the materials are combined in the order above by mixing. The composition is topically applied to the skin for exfoliation.

EXAMPLE II

A composition, according to the present invention is prepared as follows:

| Material | Weight % |
|---|---|
| Phase I | |
| Purified Water | 50.0 |
| Sodium Dehydroacetate | 0.1 |
| Pantethine | 0.1 |
| Hyaluronic Acid | 0.2 |
| Purified Water | 4.0 |
| Steareth-20 | 3.0 |
| Purified Water | 10.0 |
| N-acetyl-D-Glucosamine | 1.0 |

-continued

| Material | Weight % |
| --- | --- |
| Urea | 5.0 |
| Dimethicone | 5.0 |
| Cyclomethicone | 15.0 |
| Tocopheryl Acetate | 0.5 |
| Polyacrylamide | 2.0 |
| Butylene Glycol | 1.0 |
| Purified Water | 2.0 |
| Citric Acid | 0.1 |
| Pigment | 1.0 |

To prepare the composition, the materials are combined in the order above by mixing. The composition is topically applied to the skin for exfoliation.

EXAMPLE III

A composition according to the present invention, containing N-acetyl-D-glucosamine, is studied to determine the effect on desquamation. A panel of individuals is selected to participate in the test. The selected participants are 15 females between ages 21 and 65 years. Participants are given the composition to take home and self administer on their right hand two times a day, once in the morning after washing and once in the evening at least 15 minutes before bedtime for 4 weeks. The left hand is the untreated control sample. Participants are allowed to use only the composition being studied and are to log its use in a daily diary. At intervals of 2 and 4 weeks, the participants return for testing without applying the composition for at least 12 hours. The participants are tested without moisturizer or any other product on the skin of their hands. Their skin is acclimated to an environment of about 70° F., and about 40 percent relative humidity for about 20 minutes.

Skin exfoliation is measured with D-Squame discs and image analysis. Specifically, the amount of flakes removed from the skin surface using D-Squame discs are measured. Firmly and evenly, 4 D-Squame discs are pressed on the back of each hand using a hand held uniform pressure device. The discs are removed by gently pulling them away from the skin. After removal, the discs are mounted on clear microscope slides and evaluated with an image analyzer, OPTIMA. A camera takes a picture of the slide and the average gray value is measured to determine the corresponding density of stratum corneocytes. Denser samples have higher gray value differences.

Results show that the composition reduces skin flakiness after 2 weeks and 4 weeks of treatment when compared to untreated control hand area. After 2 weeks there is about a 15.8 percent decrease and after 4 weeks there was about 16.3 percent decrease in skin flakiness, thereby showing its utility in desquamation.

What we claim is:

1. A method for exfoliation of the skin comprising applying to the skin a composition comprising an exfoliating-effective amount of an amino sugar selected from the group consisting of N-acetyl-D-glucosamine, N-acetylgalactosamine, and a combination thereof.

2. The method according to claim 1 wherein the amino sugar is present in an amount from about 0.01 percent to about 25.0 percent of the weight of the composition.

3. The method according to claim 2 wherein the amino sugar is present in an amount from about 0.5 percent to about 10.0 percent of the weight of the composition.

4. The method according to claim 3 wherein the amino sugar is present in an amount from about 1.0 percent to about 5.0 percent of the weight of the composition.

5. The method according to claim 1 wherein the composition is applied to the skin for a period of at least 4 months.

6. The method according to claim 5 wherein the composition is applied weekly.

7. The method according to claim 1 wherein the composition is applied to the skin for a period of at least 2 months.

8. The method according to claim 1 wherein the compositions are applied from about 4 to about 5 times a week.

9. The method according to claim 8 wherein the composition is applied two times a day.

10. The method according to claim 1 wherein the composition further comprises chitin.

* * * * *